(12) United States Patent
Richards et al.

(10) Patent No.: US 10,918,663 B2
(45) Date of Patent: Feb. 16, 2021

(54) COMPOSITIONS AND METHODS FOR THE TREATMENT OF BACTERIAL VAGINOSIS

(71) Applicant: Reoxcyn, LLC, Pleasant Grove, UT (US)

(72) Inventors: Kurt Richards, Herriman, UT (US); Jeffrey Mocny, Durham, NC (US)

(73) Assignee: REOXCYN, LLC, South Jordan, UT (US)

( * ) Notice: Subject to any disclaimer, the term of this patent is extended or adjusted under 35 U.S.C. 154(b) by 0 days.

(21) Appl. No.: 16/126,218

(22) Filed: Sep. 10, 2018

(65) Prior Publication Data

US 2019/0298760 A1 Oct. 3, 2019

Related U.S. Application Data

(60) Provisional application No. 62/651,852, filed on Apr. 3, 2018.

(51) Int. Cl.
| | |
|---|---|
| *A61K 33/20* | (2006.01) |
| *A61P 15/02* | (2006.01) |
| *A61K 47/32* | (2006.01) |
| *A61K 47/02* | (2006.01) |

(52) U.S. Cl.
CPC .............. *A61K 33/20* (2013.01); *A61K 47/02* (2013.01); *A61K 47/32* (2013.01); *A61P 15/02* (2018.01)

(58) Field of Classification Search
CPC ...................................................... A61P 15/02
See application file for complete search history.

(56) References Cited

U.S. PATENT DOCUMENTS

| | | | |
|---|---|---|---|
| 6,607,753 B2 * | 8/2003 | Alexis .................... | A61P 31/12 424/725 |
| 9,474,768 B1 * | 10/2016 | Richards ............... | A61K 47/34 |
| 2016/0101115 A1 * | 4/2016 | Crapo .................. | A61K 31/555 514/184 |

* cited by examiner

*Primary Examiner* — Gina C Justice
(74) *Attorney, Agent, or Firm* — Knobbe, Martens, Olson & Bear LLP

(57) ABSTRACT

Described herein are methods and formulations for treating, inhibiting, or ameliorating vaginitis, including bacterial vaginosis. Aspects described herein relate to formulations including a reactive oxygen species, a rheology agent, and a silicone polymer and methods of using these formulations for treating, ameliorating, or inhibiting a vaginitis, including bacterial vaginosis.

23 Claims, 9 Drawing Sheets

COMPOSITIONS AND METHODS FOR THE TREATMENT OF BACTERIAL VAGINOSIS

RELATED APPLICATIONS

This application claims the benefit of priority to U.S. Provisional Patent Application No. 62/651,852, filed on Apr. 3, 2018, the disclosure of which is incorporated by reference herein in its entirety.

FIELD

The present disclosure relates to methods and compositions for treating, inhibiting, or ameliorating vaginal infections, including bacterial vaginosis, or symptoms of vaginal infections, including symptoms of bacterial vaginosis. Specifically, the present disclosure relates to formulations including reactive oxygen species, rheology agents, and silicone polymers for promoting healthy vaginal microenvironment, and methods of using the formulations for the care of the vaginal region.

BACKGROUND

Bacterial vaginosis is the most common vaginal infection worldwide and the most common cause of vaginal irritation, discharge, and malodor. It is estimated that the prevalence of bacterial vaginosis is 30% in the United States, 44% in sub-Saharan Africa, and 10% in Australia. Bacterial vaginosis is linked to serious health problems such as preterm birth, post-operative infection, and increased susceptibility to HIV and other sexually transmitted infections.

Bacterial vaginosis is caused by an imbalance of naturally occurring bacterial microbiota and can be microbiologically characterized by replacement of the lactobacilli-predominant vaginal microbiota by potential pathogenic vaginal bacteria. The vaginal microflora changes from one in which normally plentiful *Lactobacillus* species are scarce and other anaerobic bacteria, such as *Gardnerella vaginalis, Mobiluncus* species, *Atopobium vaginae*, and *Prevotella* species are plentiful. The change from a healthy, $H_2O_2$ and lactic acid producing lactobacilli-dominated microbiota to a complex multispecies microbiota can occur relatively quickly and results in bacterial vaginosis.

Current treatments of bacterial vaginosis include antibiotics. However, antibiotics are becoming less effective because of resistant bacteria. In addition, antibiotics can have significant side effects. For example, some antibiotics carry a potential risk of carcinogenicity and cause nausea, abdominal cramps, vomiting, headaches, and flushing. There is also a high incidence of fungal infection, such as *Candida albicans*, during antibiotic treatment of bacterial vaginosis. There is a need for treatments that are not systemically absorbed and also minimize systemic or local adverse effects.

Some recognized difficulties with treatment of bacterial vaginosis are that current antibiotic treatment does not always distinguish between the bacteria normally present in healthy vaginal microflora and the infecting anaerobes, and not all anaerobes present are necessarily susceptible to the same antibiotic. There is a need for treatment for bacterial vaginosis that has some selectivity for activity against unwanted bacteria and no or low activity against normal vaginal microflora. In particular, there is a need for a treatment that reduces the levels of harmful Gram negative bacteria while concomitantly not inhibiting re-establishment of *Lactobacillus* species such as lactic acid-producing or hydrogen peroxide-producing lactobacilli.

Another difficulty is that after treatment, bacterial vaginosis often recurs. Based on the results of recent clinical trials, about two thirds of patients suffer from multiple episodes of bacterial vaginosis. Because the prevalence of bacterial vaginosis is 30% in the U.S., 20% of women in the U.S. have recurrent bacterial vaginosis. Furthermore, recurrent treatment with antibiotics leads to increased incidence of antibiotic resistant bacteria and reduced effectiveness of treatment. There is therefore a need for a therapy for prophylaxis of recurrence of bacterial vaginosis.

SUMMARY

It is therefore an aspect of this disclosure to provide pharmaceutical compositions and methods of using the compositions for the treatment, prophylaxis, amelioration, or inhibition of vaginal infections cancer, including bacterial vaginosis and for the treatment, prophylaxis, amelioration, or inhibition of symptoms of vaginal infections, including bacterial vaginosis.

Some embodiments provided herein relate to a method of promoting vaginal health in a subject. In some embodiments, the method includes topically administering to a vaginal region of a subject a composition promoting a healthy vaginal microenvironment by maintaining healthy vaginal microbiota. In some embodiments, the composition includes a reactive oxygen species, a rheology agent, a silicone polymer, and a pH adjuster. In some embodiments, the composition further includes water. In some embodiments, the composition includes hypochlorite in an amount of about 60 ppm, sodium magnesium silicate in an amount of about 3% w/v, dimethicone in an amount of about 10% w/v, hydrochloric acid in an amount of about 0.08% w/v, and water in an amount of about 90% w/v.

In some embodiments, the reactive oxygen species is ozone, peroxide, active chlorine, active oxygen, superoxide, active hydrogen, hydroxyl radical, or singlet oxygen. In some embodiments, the reactive oxygen species is hypochlorite. In some embodiments, the reactive oxygen species is present in an amount of about 50 to about 100 ppm. In some embodiments, the reactive oxygen species is present in an amount of about 60 ppm. In some embodiments, the reactive oxygen species is present in an amount of about 75 ppm.

In some embodiments, the rheology agent is a metal silicate. In some embodiments, the rheology agent is sodium magnesium silicate. In some embodiments, the rheology agent is Laponite™. In some embodiments, the rheology agent is Laponite XL21™, Laponite RD™, Laponite RDS™, Laponite S482™, Laponite SL25™, Laponite EP™, Laponite JS™, Laponite XLS™, Laponite D™, or Laponite XLG™. In some embodiments, the rheology agent is present in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v or any percentage or range therebetween. In some embodiments, the rheology agent is present in an amount of about 3% w/v.

In some embodiments, the silicone polymer is amodimethicone, cyclo-dimethicone, cyclomethicone, dimethicone 500, dimethicone satin, iso-dimethicone copolymer, or blends thereof. In some embodiments, the silicone polymer is present in an amount of about 0.5%, 1%, 5%, 10%, 15%, 20%, 30%, 40%, or 50% w/v or any percentage or range therebetween. In some embodiments, the silicone polymer is present in an amount of about 10% w/v.

In some embodiments, the pH adjuster is sodium hydroxide, nitric acid, sodium acetate, hydrochloric acid, acetate buffer, citrate buffer, or phosphate buffer. In some embodiments, the pH adjuster is present in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v or any percentage or range therebetween. In some embodiments, the pH adjuster is present in an amount of about 0.08% w/v.

In some embodiments, the method further includes administering a compound common for treatment of vaginitis. In some embodiments, the compound is an antimicrobial, an anti-inflammatory, or an antihistamine. In some embodiments the antimicrobial is an antibiotic or an antifungal. In some embodiments, the antibiotic is metronidazole or clindamycin. In some embodiments the antifungals is azole, naftifine, ciclopirox, or terbinafine. In some embodiments, the antimicrobial agent is administered topically as a cream, a lotion, gel, or other formulation for topical administration. In some embodiments, the antimicrobial agent is administered orally.

In some embodiments, the method includes preventing or treating bacterial vaginosis. In some embodiments, the healthy vaginal microbiota comprises bacteria of the genus *Lactobacillus*. In some embodiments, the method further includes reducing secretion of pro-inflammatory cytokines from vaginal epithelial cells. In some embodiments, the pro-inflammatory cytokine is IL-8. In some embodiments, the method further includes preventing an inflammatory response in a vaginal microenvironment.

In some embodiments, the method further includes activating a nuclear factor-like 2 (Nrf2) related pathway. In some embodiments, the activation of Nrf2 related pathway prevents oxidative damage. In some embodiments, the method further includes increasing glutathione secretion in a vaginal microenvironment.

BRIEF DESCRIPTION OF THE DRAWINGS

FIG. 1A illustrates the vaginal microenvironment of prepuberal girls. FIG. 1B illustrates the vaginal microenvironment of adult women. FIG. 1C illustrates the vaginal microenvironment of postmenopausal women. As shown, the vaginal microenvironment is a complicated ecosystem that changes with age. Healthy vaginal microbiota is dependent on hormone maintenance and populations of *Lactobacillus* species for homeostasis.

DETAILED DESCRIPTION

Figure 1A:
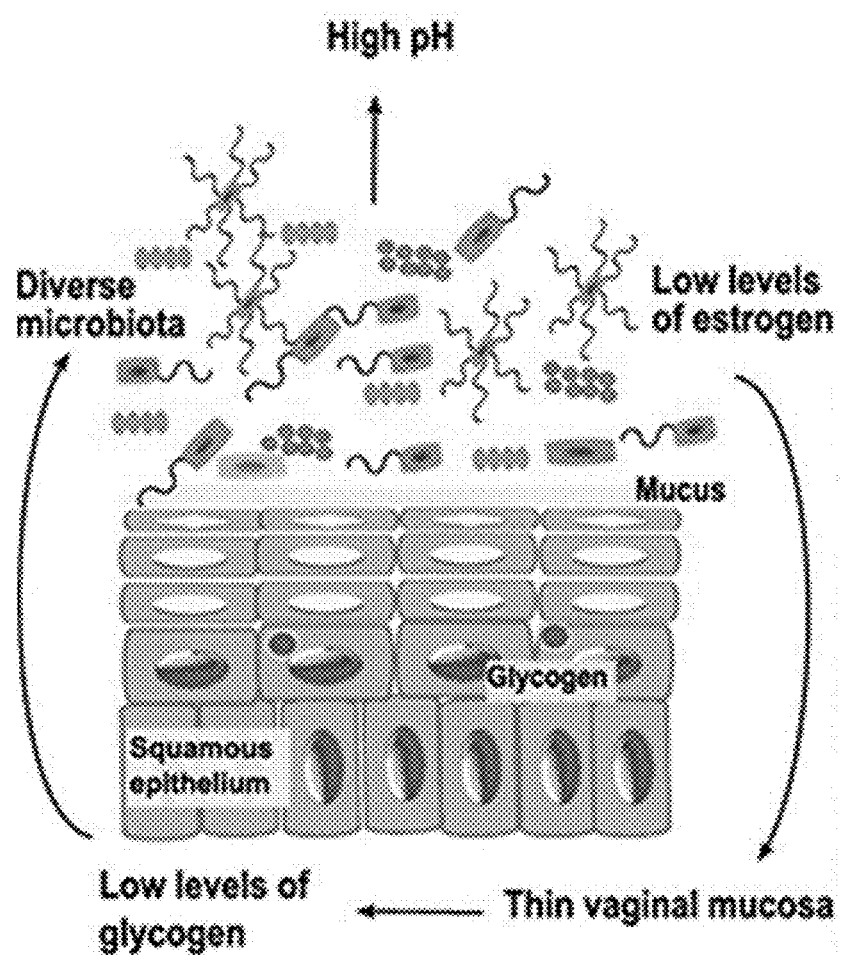
FIGS. 1A-1C illustrate the vaginal microenvironment.

Embodiments provided herein relate to methods and compositions for the treatment of vaginal infections, including bacterial vaginosis. The methods of treating a vaginal infection, such as bacterial vaginosis, include administering to a subject in need a therapeutically effective amount of a composition including a reactive oxygen species, a rheology agent, a silicone polymer, and a pH adjuster. Also provided are compositions that include a reactive oxygen species, a rheology agent, a silicone polymer, and a pH adjuster.

It will be readily understood that the aspects of the present disclosure, as generally described herein, can be arranged, substituted, combined, separated, and designed in a wide variety of different configurations, all of which are explicitly contemplated herein.

Unless defined otherwise, technical and scientific terms used herein have the same meaning as commonly understood by one of ordinary skill in the art to which the present disclosure belongs. All patents, applications, published applications and other publications referenced herein are expressly incorporated by reference in their entireties unless stated otherwise. For purposes of the present disclosure, the following terms are defined below.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. When a value is preceded by the term about, the component is not intended to be limited strictly to that value, but it is intended to include amounts that vary from the value.

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, a "subject" or a "patient" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternatives, the subject is human.

Some embodiments disclosed herein relate to selecting a subject or patient in need. In some embodiments, a patient is selected who is in need of treatment, amelioration, inhibition, progression, prophylaxis, or improvement in disease symptoms or who is in need of curative therapy. In some embodiments, a patient is selected who has symptoms of vaginitis, including symptoms of bacterial vaginosis. In some embodiments, a patient is selected who has been diagnosed with vaginitis, such as a patient who has been diagnosed with bacterial vaginosis. Such identification or selection of said subjects or patients in need can be made through clinical and/or diagnostic evaluation.

As used herein, the term "treatment" refers to an intervention made in response to a disease, disorder or physiological condition manifested by a subject, particularly a subject suffering from vaginitis, such as bacterial vaginosis. The terms treating, treatment, therapeutic, or therapy do not necessarily mean total cure or abolition of the disease or condition. The aim of treatment may include, but is not limited to, one or more of the prophylaxis of the infection, alleviation or prevention of symptoms, slowing or stopping the progression or worsening of the infection, curative treatment of the infection, or the remission of the infection. In some embodiments, treatment refers to both treatment of the underlying disease or treatment of the disease symptoms. For example, in some embodiments, treatments reduce, alleviate, ameliorate, or eradicate the symptom(s) of the disease and/or provide curative therapy of the disease.

The term "therapeutically effective amount" is used to indicate an amount of a composition that elicits the biological or medicinal response indicated. For example, a therapeutically effective amount of composition can be the amount needed to prevent, alleviate, or ameliorate symptoms of disease. This response may occur in a tissue, system, animal, or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The bacterial vaginosis formulations described herein may be administered to a subject in need in a therapeutically effective amount. The therapeutically effective amount may be in an amount to prevent growth of bacteria. For example, the therapeutically effective amount may be an amount that is of the minimum inhibitory concentration (MIC). As used herein, "MIC" is the lowest concentration of a chemical which prevents visible growth of a bacterium. The MIC of a formulation may be determined by preparing solutions of the formulation in vitro at increasing concentrations, incubating the formulations with the separate batches of cultured bacteria, and measuring the results using agar dilution or broth microdilution. A MIC depends on the microorganism, the affected human being (in vivo only), and the components in the formulation.

The term "vaginitis" refers to infection or inflammation of the vagina caused by pathogens, including, for example, bacteria, fungi, or viruses. In general vaginitis is defined as a spectrum of conditions causing vulvovaginal symptoms such as itching, burning, irritation, malodor, and abnormal discharge. Vaginitis according to this disclosure, in particular includes bacterial vaginosis, *Candida* vaginitis, *Trichomonas* vaginitis, including recurrent types of the aforementioned infections.

As used herein, the term "bacterial vaginosis" refers to a type of polymicrobial clinical syndrome resulting from replacement of the normal hydrogen peroxide producing *Lactobacillus* species in the vagina with high concentrations of anaerobic bacteria (e.g., *Prevotella* or *Mobiluncus*), *Gardnerella vaginalis, Ureaplasma, Mycoplasma*, and numerous fastidious or uncultivated anaerobes. Some women experience transient vaginal microbial changes, whereas others experience them for a longer interval of time. Among women presenting for care, bacterial vaginosis is the most prevalent cause of vaginal discharge or malodor; however, in a nationally representative survey, most women with bacterial vaginosis were asymptomatic. The cause of the microbial alteration that characterizes bacterial vaginosis is not fully understood, nor is whether bacterial vaginosis results from acquisition of a sexually transmitted pathogen. Nonetheless, women with bacterial vaginosis are at increased risk for the acquisition of some sexually transmitted diseases (STDs; e.g., HIV, *N. gonorrhoeae, C. trachomatis*, or HSV-2), complications after gynecologic surgery, complications of pregnancy, and recurrence of bacterial vaginosis.

As used herein, the term "microflora" refers to microorganisms of a particular habitat or host organism, and vaginal microflora refers to microorganisms of the vaginal region.

As used herein, the term "healthy vaginal microflora" refers to a microflora state that is not associated with any vaginal condition or disease. Healthy vaginal microflora is usually dominated by Lactobacilli. Several *Lactobacillus* species, including *L. jensenii, L. gasseri, L. iners*, and *L. crispatus* are considered to be major or dominant vaginal Lactobacilli. They are frequently accompanied by less abundant minor *Lactobacillus* species including *L. acidophilus, L. johnsoni, L. vaginalis, L. fermentum, L. reuteri*, etc. The numerical prevalence of Lactobacilli in the vagina prevents its colonization by other pathogens. Many important aspects of women's sexual and reproductive health rely on the protective role of Lactobacilli in the vaginal environment.

As used herein, the term "abnormal vaginal microflora" refers to a microflora state that is associated with certain vaginal conditions or diseases. Abnormal vaginal microflora associated with bacterial vaginosis has a number of distinct characteristics, including replacement of *Lactobacillus* by fastidious anaerobic bacteria. Such microorganisms include *Gardnerella vaginalis, Atopobium vaginae, Megasphaera*, and BVAB2, which frequently dominate abnormal vaginal microflora during the development of bacterial vaginosis or the transition towards bacterial vaginosis.

As used herein, "pro-inflammatory cytokines" refers to cytokines that promote systemic inflammatory reactions. Pro-inflammatory cytokines can include, for example, interferon gamma (IFN-$\gamma$), monocyte chemoattractant protein 1 (MCP-1), tumor necrosis factors (including TNF-$\alpha$), interleukins (including IL-1, IL-4, IL-6, IL-8, IL-10, IL-12, and IL-18), and granulocyte-macrophage colony-stimulating factor (GM-CSF).

Some embodiments provided herein relate to bacterial vaginosis formulations that include a reactive oxygen species, a rheology agent, a silicone polymer, and a pH adjuster. In some embodiments, the formulation is administered topically to a vaginal region. In some embodiments, the composition is administered in combination with a vaginitis therapy, including antimicrobial agents, anti-inflammatory agents, or antihistamines, which may be formulated for topical or oral administration.

As used herein, the term "reactive oxygen species (ROS)" refers to chemically reactive molecules containing oxygen. Examples include ozone, peroxides, active chlorines, active oxygens, superoxides, active hydrogens, hydroxyl radical, and singlet oxygen. ROS are formed as a natural byproduct of the normal metabolism of oxygen and have important roles in cell signaling and homeostasis. In some embodiments, a reactive oxygen species is hypochlorite.

ROS can include, but are not limited to superoxides ($O_2^{*-}$, $HO_2^*$), hypochlorites ($OCl—$, $HOCl$, $NaClO$), hypochlorates ($HClO_2$, $ClO_2$, $HClO_3$, $HClO_4$), oxygen derivatives ($O_2$, $O_3$, $O_4^{*-}$, $1O$), hydrogen derivatives ($H_2$, $H—$), hydrogen peroxide ($H_2O_2$), hydroxyl free radical ($OH^{*-}$), ionic compounds ($Na+$, $Cl-$, $H+$, $OH-$, $NaCl$, $HCl$, $NaOH$), chlorine ($Cl2$), water clusters ($n*H2O$-induced dipolar layers around ions), and combinations thereof. Some ROS can be electron acceptors and some can be electron donors.

"Hypochlorous acid", as used herein, refers to a weak acid having the chemical formula HClO. Hypochlorous acid is also known as chloric (I) acid, chloranol, or hydroxidochlorine. Salts of hypochlorite are also referred to herein and can include sodium hypochlorite (NaClO), calcium hypochlorite ($Ca(ClO)_2$), or potassium hypochlorite (KClO). Hypochlorite, or acids and salts thereof, may be used in the bacterial vaginosis formulations of the present disclosure at an amount of about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 1%, 5%, 10%, 15%, 20%, 25%, 30%, 40%, 50%, or greater w/v %, or within a range defined by any two of the aforementioned amounts. In some embodiments, the w/v % of hypochlorite or an acid or salt thereof is about 0.06% w/v. In some embodiments, the hypochlorite salt or hypochlorous acid is added directly to a bacterial vaginosis formulation. In some embodiments, the final amount of hypochlorous acid is less than, greater than, or equal to about 10, 15, 20, 25, 30, 35, 40, 45, 50, 55, 60, 65, 70, 75, 80, 85, 90, 95, 100, 120, 150, 175, 200, 300 ppm or within a range defined by any two of the aforementioned amounts. In some embodiments, the amount of hypochlorous acid in the bacterial vaginosis formulation is between about 50 to about 100 ppm. In some embodiments, the amount of hypochlorous acid in the bacterial vaginosis formulation is about 60 ppm. In some embodiments, the amount of hypochlorous acid in the bacterial vaginosis formulation is about 75 ppm.

As used herein, the term "rheology agent" refers to a substance that modulates the viscosity of the bacterial vaginosis formulation, without modifying other properties of the formulation. In some embodiments, the rheology agent acts as a thickener by increasing the viscosity of the bacterial vaginosis formulation. In some embodiments, the rheology agent can include a metal silicate. In some embodiments, the rheology agent is sodium magnesium silicate, a silicate of sodium and magnesium. In some embodiments, sodium magnesium silicate is a synthetic silicate clay, having magnesium and sodium silicate. In some embodiments, a rheology agent is used as a binder and bulking agent in cosmetics and personal care products, in part because of its ability to absorb water. Sodium magnesium silicate is effective in slowing the decomposition of formulas, and can prevent premature darkening of compositions and prevent premature development of a foul odor, thereby improving the shelf life of cosmetic compositions. In some embodiments, the sodium magnesium silicate is Laponite, including for example, Laponite XL21™, Laponite RD™, Laponite RDS™, Laponite S482™, Laponite SL25™, Laponite EP™, Laponite JS™, Laponite XLS™, Laponite D™, or Laponite XLG™. The rheology agent may be used in the bacterial vaginosis formulation in an amount of about 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of rheology agent is about 3% w/v.

In some embodiments, a rheology agent is added in any suitable fashion to prepare the formulation. For example, the rheology agent can be mixed with the formulation to form a viscous solution before other components are added. In some instances, the rheology agent can be added into the formulation as the solution is being mixed to allow for even dispersion of the rheology agent. In other instances, purified water or any other suitable solution can be added to the formulation and rheology agent to achieve the desired viscosity.

In some embodiments, adding rheology agent may be in any suitable amount to achieve the desired viscosity of the formulation. For example, the weight percent of the rheology agent may be 0.1%, 0.25%, 0.5%, 0.75%, 1%, 1.5%, 2%, 2.5%, 3%, 3.5%, 4%, 4.5%, 5%, 6%, 7%, 10%, 15%, or greater w/v %, or in an amount within any two of the aforementioned values or between a range defined by these values. In some embodiments, the amount of rheology agent is about 3% w/v. These weight percentages can be approximate and can be modified to achieve specific characteristics desired and/or required in the formulation.

In some embodiments, the rheology agent is added to the formulation at any suitable temperature and/or at any suitable pH. For example, in some cases, a lower temperature may result in longer hydration times for the rheology agent. Likewise, in some cases, a higher temperature may result in shorter hydration times. Therefore, in some instances, the temperature can be tailored to provide a suitable hydration time to prepare the formulation. In other embodiments, the pH of the rheology agent and formulation is adjusted to achieve suitable hydration of the rheology agent. For example, in the case of acrylic acid polymers, the mixture can be neutralized by addition of a strong base to form a polymer salt to achieve a suitable viscosity. In yet other embodiments, copolymers are added to the rheology agent to achieve a suitable viscosity. For example, copolymers such as allyl sucrose and/or allylpentaerythritol can be added to achieve a suitable viscosity.

As used herein, silicone polymers include dimethicone, which is also known as polydimethylsiloxane (PDMS), dimethylpolysiloxane, E900, or polymerized siloxane and has the chemical formula of $CH_3[Si(CH_3)_2O]_nSi(CH_3)_3$ where n is the number of repeating monomer $[Si(CH_3)_2]$ units. Silicone polymers also include cyclomethicone, which is a cyclic siloxane. In some embodiments, the silicone polymer used in the bacterial vaginosis formulation is a blend of dimethicone and cyclomethicone. In some embodiments, the silicone polymer is dimethicone satin, a mixture of low and high molecular weight linear silicones. In some embodiments, the silicone polymer is amodimethicone, cyclo-dimethicone, cyclomethicone, dimethicone 500, dimethicone satin, iso-dimethicone copolymer, or blends thereof. In some embodiments, a silicone polymer acts as a moisturizer, a slip agent, or a lubricant. The silicone polymer may be used in the bacterial vaginosis formulation in an amount of about 0.5%, 1%, 5%, 10%, 15%, 20%, 30%, 40%, 50%, or greater w/v %, or in an amount within any two of the aforementioned values or between a range defined by these values. In some embodiments, the amount of silicone polymer is about 10% w/v.

As used herein, the term "pH adjuster" refers to an acid, base, or buffer that may be used to change the pH of the formulation. A pH adjuster includes sodium hydroxide, nitric acid, sodium acetate, hydrochloric acid, or various buffers, such as acetate, citrate, or phosphate buffers. In some embodiments, the pH adjuster is hydrochloric acid. In some embodiments, the pH adjuster is present in an amount of about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v, or an amount within a range defined by any two of the aforementioned values. In some embodiments, the pH adjuster is present in an amount of about 0.08% w/v. As used herein, the pH of the composition is the numerical scale to specify the acidity or basicity of the formulation. In some embodiments, the pH of the formulation is about 5.0, 5.5, 6.0, 6.5, 6.6, 6.7, 6.8, 6.9, 7.0, 7.1, 7.2, 7.3, 7.4, 7.5, 7.6, 7.7, 7.8, 7.9, 8.0, or 8.5, or within a ranged defined by any two of the aforementioned values. In some embodiments, the pH of the formulation is in a range from about 6.0 to about 7.5.

As used herein, "tonicity" refers to osmotic pressure of a composition to cause water movement. Tonicity is measured in osmoles, which is defined by the number of moles of a chemical compound that contribute to a solution's osmotic pressure. In various embodiments, the bacterial vaginosis formulations described herein have a tonicity of between about 1 milli-osmoles and 100 osmoles. By tonicity of between about 1 milli-osmoles and 100 osmoles, it is meant that all hundredth, tenth and integer unit amounts within the range are specifically disclosed as part of the invention. Tonicity can be classified in terms of isotonic, hypertonic, or hypotonic. Thus, for example, a "1x" tonicity refers to a solution that is isotonic relative to normal human blood and cells. Solutions that are hypotonic or hypertonic in comparison to normal human blood and cells are described relative to a 1× solution using an appropriate multiplier. For example, a hypotonic solution may have 0.1×, 0.25× or 0.5× tonicity, and a hypertonic solution may have 2×, 3×, 4×, 5×, 6×, 7×, 8×, 9× or 10× tonicity. The bacterial vaginosis formulations described herein may be hypotonic, isotonic, or hypertonic as desired. For example, any of the pharmaceutical formulations described herein may have about 0.1× tonicity, about 0.25× tonicity, about 0.5× tonicity, about 1× tonicity, about 2× tonicity, about 3× tonicity, about 4× tonicity, about 5× tonicity, about 6× tonicity, about 7× tonicity, about 8× tonicity, about 9× tonicity, about 10× tonicity, at least about 1× tonicity, at least about 2× tonicity, at least about 3× tonicity, at least about 4× tonicity, at least about 5× tonicity, at least about 6× tonicity, at least about 7× tonicity, at least about 8× tonicity, at least about 9× tonicity, at least about 10× tonicity, between about 0.1× to about 1×, between about 0.1× to about 0.5×, between about 0.5× to about 2×, between about 1× to about 4×, between about 1× to about 2×, between about 2× to about 10×, or between about 4× to about 8×.

Osmolality is a measure of the number of dissolved particles in a fluid and is measured as mOsm/kg. In some embodiments, the bacterial vaginosis formulations described herein have osmolality measurement values of about 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, 55, 60, 65, 70, 80, 90, or 100 mOsm/kg, or within a range defined by any two of the aforementioned values. In some embodiments, the bacterial vaginosis formulations have osmolality measurement vales of about 3 to 5 mOsm/kg.

The bacterial vaginosis formulations described herein may further include an additive known in the art. Exemplary additives include emollients, moisturizers, humectants, pigments, dyes, pearlescent compounds, nacreous pigments, bismuth oxychloride coated mica, titanium dioxide coated mica, colorants, fragrances, biocides, preservatives, alpha hydroxy acids, antioxidants, anti-microbial agents, antifungal agents, antiperspirant agents, exfoliants, hormones, enzymes, medicinal compounds, vitamins, salts, electrolytes, alcohols, polyols, polypropylene glycol, polyisobutene, polyoxyethylene, behenic acid, behenyl, sugar-alcohols, absorbing agents for ultraviolet radiation, botanical extracts, surfactants, silicone oils, organic oils, waxes, alkaline or acidic or buffering agents, film formers, thickening agents, hyaluronic acid, fumed silica, hydrated silica, talc, kaolin, starch, modified starch, mica, nylon, clay, bentonite, organo-modified clays, and combinations thereof.

The bacterial vaginosis formulations provided herein may be prepared, packaged, or sold in formulations for topical administration. The formulations can be filled into suitable packaging (containers) such as, for example, tubes, cartons, capsule, jars, bottles, canisters, squeeze pack, pouches, packages, packets, sacks, tank, or other containers. In some embodiments, the formulation may be applied directly to the vaginal region. In some embodiments, the formulation may be applied on a condom, an applicator, or other device for application to the vaginal region.

Packaging can include single use aliquots in single use packaging such as pouches. The formulation can be packaged in suitable packaging having volumes of about 0.1 oz., about 0.2 oz., about 0.5 oz., about 1 oz., about 2 oz., about 4 oz., about 8 oz., about 16 oz., about 32 oz., about 48 oz., about 64 oz., about 80 oz., about 96 oz., about 112 oz., about 128 oz., about 144 oz., about 160 oz., or any range created using any of these values. The plastic bottles can also be plastic squeezable pouches having similar volumes.

In some embodiments, packaging is generally free of any dyes, metal specks or chemicals that can be dissolved by acids or oxidizing agents. In other embodiments, any bottles, package caps, bottling filters, valves, lines, and heads used in packaging are specifically rated for acids and oxidizing agents. In some cases, package caps with any organic glues, seals, or other components sensitive to oxidation may be avoided since they could neutralize and weaken the product over time.

In some embodiments, the packaging used herein reduces decay of active species (such as, for example, ROS and/or RS) found within the topical formulations. In other embodiments, the packaging described does not further the decay process. In some embodiments, the packaging used can be inert with respect to the active species in the formulations. In some embodiments, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of ROS and/or RS in the composition. In one embodiment, a bottle can only result in about 3% decay/month of superoxide. In another embodiment, a pouch can only result in about 4% decay/month of superoxide.

As used herein, the term "coadministration" of pharmacologically active compounds refers to the delivery of two or more separate chemical entities, whether in vitro or in vivo. Coadministration refers to the simultaneous delivery of separate agents; to the simultaneous delivery of a mixture of agents; as well as to the delivery of one agent followed by delivery of a second agent or additional agents. In all cases, agents that are coadministered are intended to work in conjunction with each other. Similarly, in the context of administration of more than one compound, the term "in combination" refers to a concomitant delivery of one compound with one or more compounds. The compounds may be administered in combination by simultaneous administration or administration of one compound before or after administration of another compound.

In some embodiments, the bacterial vaginosis formulation is administered in combination with a vaginitis therapy, including antimicrobial agents, anti-inflammatory agents, or antihistamines. As used herein, antimicrobial agents include antibiotics or antifungals. In some embodiments, antibiotics includes aminoglycoside derivative like amikacin, gentamicin, kanamycin, neomycin, netilmicin, tobramycin, paromomycin; an ansamycin derivative like geldanamycin, herbimycin; a carbacephem derivative like loracarbef; a carbapenem derivative like ertapenem, doripenem, imipenem, meropenem; a cephalosporin derivative like cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole; a glycopeptide derivative like teicoplanin, vancomycin, telavancin; a lincosamides like clindamycin, lincomycin; a lipopeptide derivative like daptomycin; a macrolide derivative like azithromycin, clarithromycin, dirithromycin, erythromycin, roxithromycin, troleandomycin; telithreomycin, spectinomycin; a monobactam derivative like aztreonam; a nitrofuran derivative like furazolidone, nitrofurantoin; a penicillin derivative like amoxicillin, ampicillin, azlocillin, carbinicillin, cloxacillin, dicloxacillin, flucloxacillin, mezlocillin, methicillin, nafcillin, oxacillin, penicillin G, penicillin V, piperacillin, temocillin, ticarcillin; a penicillin combination like amoxicillin/clavulanate, ampicillin/sulbactam, piperacillin/tazobactam, ticarcillin/clavulanate; a polypeptide derivative like bacitracin, colistin, polymyxin B; a quinolone derivative like ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, temafloxacin; a sulfonamide derivative like mafenide, sulfonamidochrysoidine, sulfacetamide, sulfadiazine, silver sulfadiazine, sulfamethoxazole, sulfanilimide, sulfasalazine, sulfisoxazole, trimethoprim, trimethoprim/sulfamethoxazole; a tetracycline derivative like demeclocycline, doxycycline, minocycline, oxytetracycline, tetracycline; a derivative against mycobacteria like clofazimine, dapsone, capreomycin, cycloserine, ethambutol, ethioamide, isoniazid, pyrazinamide, rifampin, rifampicin, rifabutin, rifapentine, streptomycin; or arsphenamine, chloramphenicol, fosfomycin, fusidic acid, linezolid, metronidazole, mupirocin, platensimycin, quinupristin/dalfopristin, rifaximin, thiamphenicol, tigecycline, amphotericins, novobiocins, polymixins, gramicidins, framycetin, ribostamycin, arbekacin, bekanamycin (kanamycin B), dibekacin, hygromycin B, sisomicin, isepamicin, verdamicin, astromicin, neamine, ribostamycin, lividomycin, or tinidazole or any salts or variants thereof. In some embodiments, antibiotics include those that are typically used for the treatment of bacterial vaginosis, including metronidazole or clindamycin. In some embodiments, antifungals include azole, naftifine, ciclopirox, or terbinafine. In some embodiments, the antimicrobial agent is administered topically as a cream, a lotion, gel, or other formulation for topical administration. In some embodiments, the antimicrobial agent is administered orally.

As used herein "anti-inflammatory therapy" refers to a therapy that reduces inflammation. Anti-inflammatory agents include, but are not limited to, NSAIDS and glucocorticoids. Non-limiting examples of NSAIDS include aspirin, diflunisal, salsalate, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, nabumetone, diclofenac, piroxicam, meloxicam, tenoxicam, droxicam, lornoxicam, isoxicam, mefenamic acid, meclofenamic acid, flufenamic acid, tolfenamic acid, celecoxib, parecoxib, etoricoxib, lumiracoxib, fluticasone propionate/salmeterol (Advair® or Seretide®), montelukast (Singulair®), and firocoxib. Glucocorticoids include, but are not limited to, hydrocortisone, cortisone, prednisone, prednisolone, methylprednisolone, dexamethasone, betamethasone, triamcinolone, beclometasone, or fludrocortisone. In some embodiments, the anti-inflammatory agent is administered topically as a cream, a lotion, gel, or other formulation for topical administration. In some embodiments, the anti-inflammatory agent is administered orally.

As used herein, the term "antihistamine" refers to a moiety that inhibits reduces effects mediated by histamine By way of example, moieties having negative modulation of histamine receptors as their main therapeutic effect (i.e., antagonists at the histamine H1 receptor) are antihistamines. For example, chlorpheniramine, which may also have anticholinergic activity, is considered an antihistamine Antihistamine includes, for example, first generation antihistamines such as ethylenediamines, ethanolamines, alkylamines, piperazines and tricyclics. Antihistamines further include second generation antihistamines such as acrivastine, astemizole, cetirizine, loratadine, mizolastine, desloratidine and fexofenadine. In some embodiments, the antihistamine is administered topically as a cream, a lotion, gel, or other formulation for topical administration. In some embodiments, the antihistamine is administered orally.

In some embodiments, the "purity" of any given agent (for example, hypochlorous acid or a buffer) in a composition may be specifically defined. For instance, certain compositions may include, for example, an agent that is at least 80, 85, 90, 91, 92, 93, 94, 95, 96, 97, 98, 99, or 100% pure, including all decimals in between, as measured, for example and by no means limiting, by analytical chemistry techniques.

In some embodiments, the bacterial vaginosis formulation may be applied directly into the vagina, and therefore, the formulation may be formulated for topical application. Accordingly, the formulation may have any suitable form for topical administration. In some embodiments the formulation is in the form of a cream, a lotion, a gel, a liquid, a foam, or an ointment. In some embodiments, the formulation is prepared as a vaginal suppository gel. In some embodiments, the formulation is in the form of a vaginal capsule. In some embodiments, the formulation is in the form of a vaginal tablet. In some embodiments, the formulation is in the form of a suspension.

The bacterial vaginosis formulations described herein are used for the treatment of vaginitis, such as bacterial vaginosis. The formulations may be used to modulate vaginal health, to generate positive outcomes in the prevention of bacterial vaginosis, to minimize the risk for sexually transmitted infections, and to influence the vaginal microenvironment immune ecosystem.

In some embodiments, the bacterial vaginosis formulation has low osmolality values. In some embodiments, the osmolality of the bacterial vaginosis formulations is from 3-5 mOsm/kg. Typical osmolality measurements (mOsm/kg) for many topically applied compositions range from greater than 950 to 3800 mOsm/kg, significantly higher than the bacterial vaginosis formulations described herein. The low osmolality of the formulation provides a superior level of epithelial cell maintenance compared with high osmolality formulations. Low osmolality is critical for protection of epithelial layers, as the osmotic imbalance results in the dehydration of the tissues. For example, animal models tested with low osmolality formulations for cytotoxicity testing demonstrate that the formulations did not elicit a vaginal epithelia inflammation response, and there is no epithelial cell sloughing.

The bacterial vaginosis formulation also results in significantly lower cytotoxicity than other vaginitis products that are commercially available. Cytotoxicity testing in HeLa cells, for example, demonstrates that several commercially available products demonstrated death of >80% of cells in culture at dilutions of 1:5, 1:20, and 1:100 (Cunha et al. 2014. Pharmaceutics, 6, 530-542; incorporated by reference herein in its entirety). On the other hand, full strength bacterial vaginosis formulations do not demonstrate such toxicity. In comparison, bacterial vaginosis formulations offer benefit to users as a putative microbicide that augments the natural vaginal immune ecosystem.

Current treatments of bacterial vaginosis employ the use of antibiotics. However, antibiotics are becoming less effective because of resistant bacteria. In addition, antibiotics can have significant side effects. For example, some antibiotics carry a potential risk of carcinogenicity and cause nausea, abdominal cramps, vomiting, headaches, and flushing. Furthermore, antibiotic treatments are a contributing factor to bacterial vaginosis, given the indiscriminate assault of antibiotics on *Lactobacillus* species in addition to the coliforms which are typical of the infection cycle. However, the bacterial vaginosis formulations described herein enhance the natural *Lactobacillus* species by inhibiting the growth of pathogenic vaginal microbes.

The chemical-physical formulation of bacterial vaginosis compositions provided herein is designed in a way to maintain the vaginal chemistry while providing the antimicrobial function inherent to hypochlorites and maintaining a healthy osmotic balance in the tissue.

The vaginal microenvironment is a complex ecosystem containing multiple species of beneficial organisms critical for vaginal health and wellbeing. The change in microenvironment dynamics results in increases in inflammation and leaves women more susceptible to infection and STI transmission. As an example, it is suggested that higher levels of vaginal inflammation and lower levels of anti-inflammatory factors are associated with increased HIV-1 transmission across the genital mucosa (Mitchell et al. 2014. Am J Reprod Immunol. June; 71(6) 555-563; incorporated by reference herein in its entirety).

An interesting conundrum presents itself in the vaginal microenvironment. The reproductive tract itself is both an immunotolerant, and a privileged immune site at the same time as it is a mucosal surface. The mucosae functions to both initiate the adaptive immune responses, but also to prevent the immune system from responding inappropriately to the environmental antigens that reside in the urogenital tract. It is well documented that normal vaginal flora and immunity are important defense mechanisms in protection of disease, and a clear link between inflammation and subsequent infections exist.

In the vaginal microenvironment, a paucity in the normal populations of *Lactobacillus* species can result in the clinical diagnosis of bacterial vaginosis (Brotman et al. 2016. Genome Medicine. 8:35; incorporated by reference herein in its entirety). This infection is recurrent and results from the change in the microbiota where *Lactobacillus* species dominate the environment, and a subsequent reduction in the fermentation process of lactic acid production causing an elevation in pH, whereby deleterious populations of microorganisms establish a population, specifically, anaerobic bacteria (Mitchell et al. 2014. Am J Reprod Immunol. June; 71(6) 555-563).

In some embodiments, the bacterial vaginosis formulations have a neutral pH. The neutral pH of the formulation, and the absence of buffering agents will allow for the maintenance of the vaginal environment acidic pH, thereby removing a buffering effect which may complicate the infection cycle. In some embodiments, the pH of the bacterial vaginosis formulations are decreased to a slightly acidic level. In some embodiments, the slightly acidic formulation modulates normal flora, vaginal epithelial structure, and triggering of inflammation in vivo. In some embodiments, the lower pH of the formulations provides redox activity as a germicidal. In some embodiments, the lower pH of the formulation maintains redox capabilities of normal Lactobacilli flora in the reproductive tract. In some embodiments, the lower pH clears vaginal infections, including, for example *Chlamydia* infections.

The vaginal microenvironment is dominated by lactic acid bacteria which also produce reactive oxygen species such as peroxides which likely plays a significant role in the reproductive tract ability to fend off colonization by deleterious microorganisms. As evidence, pathogenic strains of the gonococcus possess significant super oxide dismutase (SOD) and catalase activity, likely due in part to the selective pressure of the vaginal microenvironment to successfully colonize. As disclosed herein, low concentrations of hypochlorites accentuate this innate immune function of the normal flora present in the reproductive tract.

These health benefits are possible with negligible irritation, and the formulation is compatible for use with condoms, further enhancing the protection from infection and safe sex practices, demonstrated by biocompatibility testing. Further testing utilizing the vaginal epithelial tissue culture models extended and confirmed these findings and demonstrated significantly lower cell toxicity compared with 1% Nonoxynol 9 (1% N9).

The bacterial vaginosis formulations disclosed herein demonstrated negligible toxicity to epithelial cells following direct contact with full strength product compared with serial dilutions of N9 demonstrated by LDH release in culture medium following exposure for 24 hours. The use of the formulations described herein results in decreased pro-inflammatory cascades given that the release of LDH is directly related to the pro-inflammatory process. Other proactive immune response markers are also observed to be decreased when exposed to the bacterial vaginosis formulation. For example, the pro-inflammatory cytokine, IL-8, and lysozyme demonstrated reduced secretion into culture medium measured by ELISA.

Taken together these results suggest that the bacterial vaginosis formulations described herein act to diminish the pro-inflammatory response at the cellular level, indicated by the reduction in these cytokines and helps to maintain the biochemical vaginal microenvironment. Accordingly, provided herein are compositions and methods for promoting a healthy vaginal microbiota, wherein the healthy vaginal microbiota is promoted by reducing secretion of pro-inflammatory cytokines in the vaginal microenvironment.

In some embodiments, the bacterial vaginosis formulations described herein modulate vaginal health by eliminating harmful bacteria, allowing natural bacteria from healthy vaginal microflora to thrive. In some embodiments, the formulations modulate vaginal health by promoting physical-chemical equilibrium in the vaginal microenvironment. In some embodiments, the bacterial vaginosis formulations include a reactive oxygen species, such as sodium hypochlorite, present in an amount ranging from about 50 to about 100 ppm. In some embodiments, the bacterial vaginosis formulations provide a germicidal capacity unlike other products that use surfactant-based approaches. The bacterial vaginosis formulations provided herein exhibit germicidal properties, and exhibit efficacy against various microbes, including N. gonorrhoeae, C. trachomatis, and Human Immuno-Virus (HIV-1). In some embodiments, the bacterial vaginosis formulations exhibit >99% reduction in microbial growth. In some embodiments, the formulation is used to prevent growth of various pathogens, including, for example, N. gonorrhoeae, C. trachomatis, HIV-1, Prevotella, Mobiluncus, Gardnerella vaginalis, Ureaplasma, Mycoplasma, S. aureus, E. coli, P. aeruginosa, C. albicans, A. niger, and other pathogens.

Figure 1B:
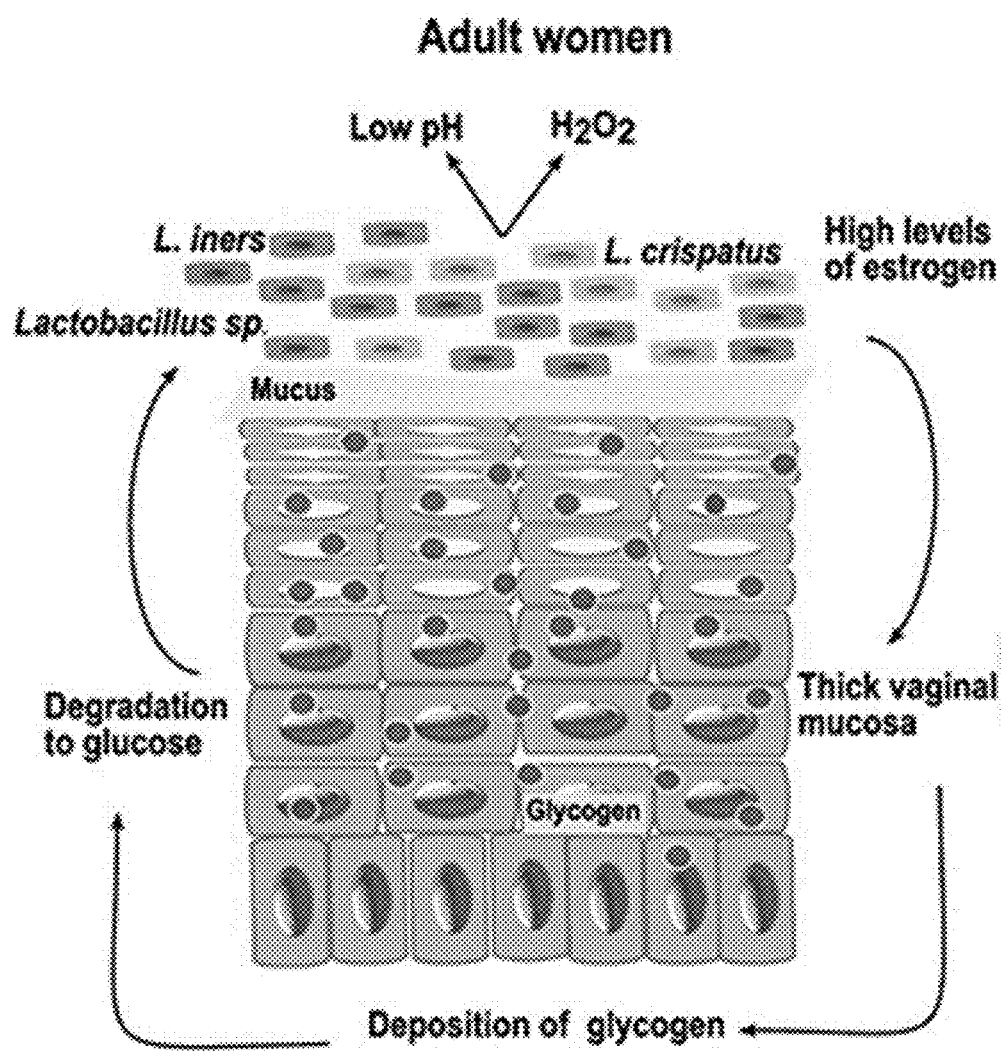
Figure 1C:
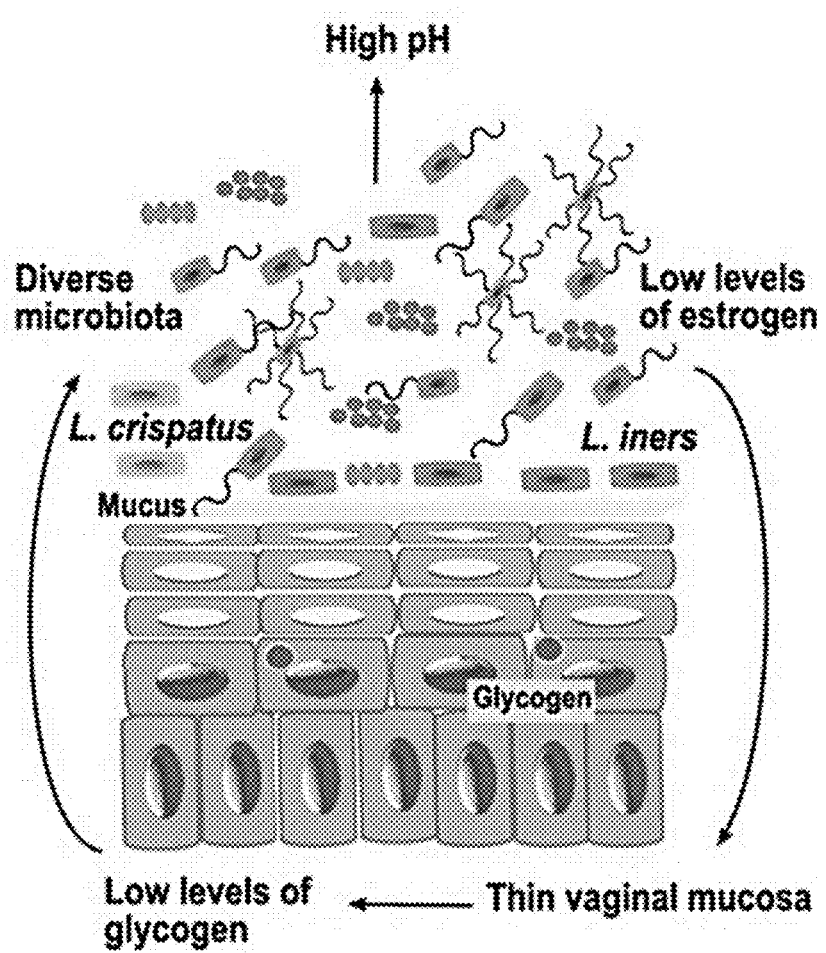

The vaginal environment is a complicated ecosystem and changes with age as illustrated in FIGS. 1A-1C. Healthy reproductive tract physiology is dependent upon hormone maintenance and populations of Lactobacillus species for homeostasis. To maintain a healthy environment, low pH and peroxides act to limit colonization by harmful or pathogenic organisms. The manipulation of the vaginal flora has been proposed as a way of maintaining a healthy reproductive tract in females to subvert bacterial vaginosis and STI infection (Brotman et al. 2016. Genome Medicine. 8:35). The use of the bacterial vaginosis formulations described herein act as both a topical anti-microbial through the redox chemical potential introduced by hypochlorites, and act to modulate the cytokine environment through hypochlorite mediated signaling to affect immunomodulation.

Studies by various authors suggests that the presence of hyper-oxide producing Lactobacilli may grant some protection from bacterial vaginosis, and that treatment of women suffering from infection responded to treatment with Lactobacillus species (Falagas et al. 2007, Clinical Microbiology and Infection. 13:7; incorporated by reference herein in its entirety). This finding suggests that part of the mechanism of immunity to vaginal infection relies on the maintenance of vaginal acidification and production of ROS. Interestingly the ROS production in healthy females does not lead to heightened inflammation, presumably modulated by redox detoxification mechanisms. Another interesting possibility is lipid chlorination resulting in anti-inflammatory signaling responses rather than traditional lipid inflammatory signaling. Therefore, modification of signaling lipids may affect the signaling properties of the cells. The bacterial vaginosis formulations described herein act to enhance the vaginal response in healthy females through activation of Nrf2 related pathways. The bacterial vaginosis formulations described herein do not elicit an IL-8 mediated inflammatory response, do not elicit cell toxicity, and also activate Nrf2.

Using a human epithelial cell model, we demonstrated that treatment with bacterial vaginosis formulations results in increased response activity by Nrf2, a global oxidative stress response transcription factor, while not causing loss in cell viability, compared to a positive tert-butylhydroquinone (tBHQ) control treatment group. This is demonstrated with the increase in glutathione (GSH) secretion in growth medium, observed in in vitro studies. Taken together, these data strengthen the hypothesis that the bacterial vaginosis formulations do not cause toxicity and that the active molecule works to prime the cell to provide strong anti-oxidant responses when exposed to conditions which may cause cellular damage. This is further supported by the finding that secretory leukocyte protease inhibitor (SLPI), a secreted protease involved with proteolytic cleavage of viral particles and pro-inflammatory peptides secretion, does not increase in the presence of the bacterial vaginosis formulations. Treatment with bacterial vaginosis formulations results in reduced IL-8 secretions from vaginal lavage. In some embodiments, the treatment reduces pro-inflammatory secretions, including decreased secretion of interferon gamma (IFN-γ), monocyte chemoattractant protein 1 (MCP-1), tumor necrosis factors (including TNF-α), interleukins (including IL-1, IL-4, IL-6, IL-8, IL-10, IL-12, and IL-18), and granulocyte-macrophage colony-stimulating factor (GM-CSF). In some embodiments, the bacterial vaginosis formulations quell an inflammatory response.

SLPI is a critical component in HIV infection, limiting the infectivity of the HIV-1 virus (Morrison et al. 2014. J Acq Immune Def Synd. 66:2, 109-117; incorporated by reference herein in its entirety). The bacterial vaginosis formulations provided herein limit the ability to infect MT-2 cells, a human T-cell leukemia cell line, following a five and ten-minute exposure, respectively. Interestingly, a reduction in the SLPI secretion in cells is observed when treated with bacterial vaginosis formulations. The reduction in SLPI is attributed to the limitation of the pro-inflammatory response in these models, as it has been shown that inflammation coupled with reduced SLPI is corollary to HIV seroconversion in females (Morrison et al. 2014. J Acq Immune Def Synd. 66:2, 109-117). The oxidative power of the bacterial vaginosis formulations reduces the infectious particles, while limiting a pro-inflammatory cascade.

Accordingly, the bacterial vaginosis formulations described herein enhance natural vaginal microflora in numerous aspects, including: pH buffering that enhances normal flora maintenance; low osmolality that results in decreased epithelial dehydration; inhibition of pro-inflammatory immune responses that leads to enhanced vaginal health; antimicrobial action that eliminates pathogens in the vaginal microenvironment causing a vaginal infection; promoting the physical-chemical equilibrium of the vaginal microenvironment; and reducing immune response cell infiltration, leading to a reduction in the inflammatory response of the vaginal microenvironment.

The disclosure is generally described herein using affirmative language to describe the numerous embodiments. The disclosure also includes embodiments in which subject matter is excluded, in full or in part, such as substances or materials, method steps and conditions, protocols, or procedures.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

Preparation of Bacterial Vaginosis Formulations

The following example describes an embodiment of a bacterial vaginosis formulation and methods of making the formulation.

A bacterial vaginosis formulation was prepared with the ingredients as provided in Table 1. The ingredients provided below were added to deionized water to a final volume of just over one liter, with a final pH adjusted to 6.5-7.0.

TABLE 1

Bacterial Vaginosis Formulation

| Ingredient | Amount | Final % wt/vol | Role in Formulation |
| --- | --- | --- | --- |
| Deionized Water | 900 mL | 90 | Base |
| Laponite XLG | 30 g | 3 | Thickening Agent |
| Dimethicone Satin | 100 mL | 10 | Moisturizer |
| Sodium Hypochlorite (4.99%) | 1.5 mL | 0.06 | ROS Molecule |
| HCl (36%) | 0.8 mL | 0.08 | pH Adjustment |

The bacterial vaginosis formulation described in Table 1 is useful for the treatment of bacterial vaginosis. The formulation may be used alone in or in combination with antibiotic therapies. Furthermore, the formulation may be applied directly to the vaginal region or may be applied with a product, such as with a condom, an applicator, or other device. The formulation may be prepared as a gel, a cream, a paste, a lotion, an ointment, or other composition suitable for topical administration to the vaginal region.

Example 2

Safety Tests for Bacterial Vaginosis Formulations

The following example describes results of studies to assess the cytotoxicity of bacterial vaginosis formulations.

The formulation described in Example 1 was tested to determine the safety of the formulation based on several safety metrics, including direct contact cytotoxicity, delayed hypersensitivity, mucosal irritation, and acute systemic toxicity. As shown in Table 2, the formulation demonstrated passing results for each metric. In addition, the formulation was tested to determine compatibility with condoms, and was found to be compatible with both natural and synthetic latex condoms using an airburst and tensile standardized testing protocol.

TABLE 2

Cytotoxicity of Bacterial Vaginosis Formulations

| Standardized Test | Result |
| --- | --- |
| Direct Contact Cytotoxicity | Passed |
| Delayed Hypersensitivity | Passed |
| Mucosal Irritation (Vaginal) | Passed |
| Acute Systemic Toxicity | Passed |
| Condom Testing: Airburst and Tensile | Compatible with natural and synthetic latex condoms |

Example 3

Cytotoxicity of Bacterial Vaginosis Formulations

The following example describes results of studies to determine the cytotoxicity of bacterial vaginosis formulations.

MatTek EpiVaginal™ tissue culture model was used to determine the cytotoxicity of the formulation described in Example 1. The culture is from normal, human-derived vaginal epithelia and dendritic cells, and is commonly used for toxicity studies. The tissue culture was exposed to the formulation for a period of 24 hours and the culture was assessed to determine cytotoxicity.

Figure 2A:
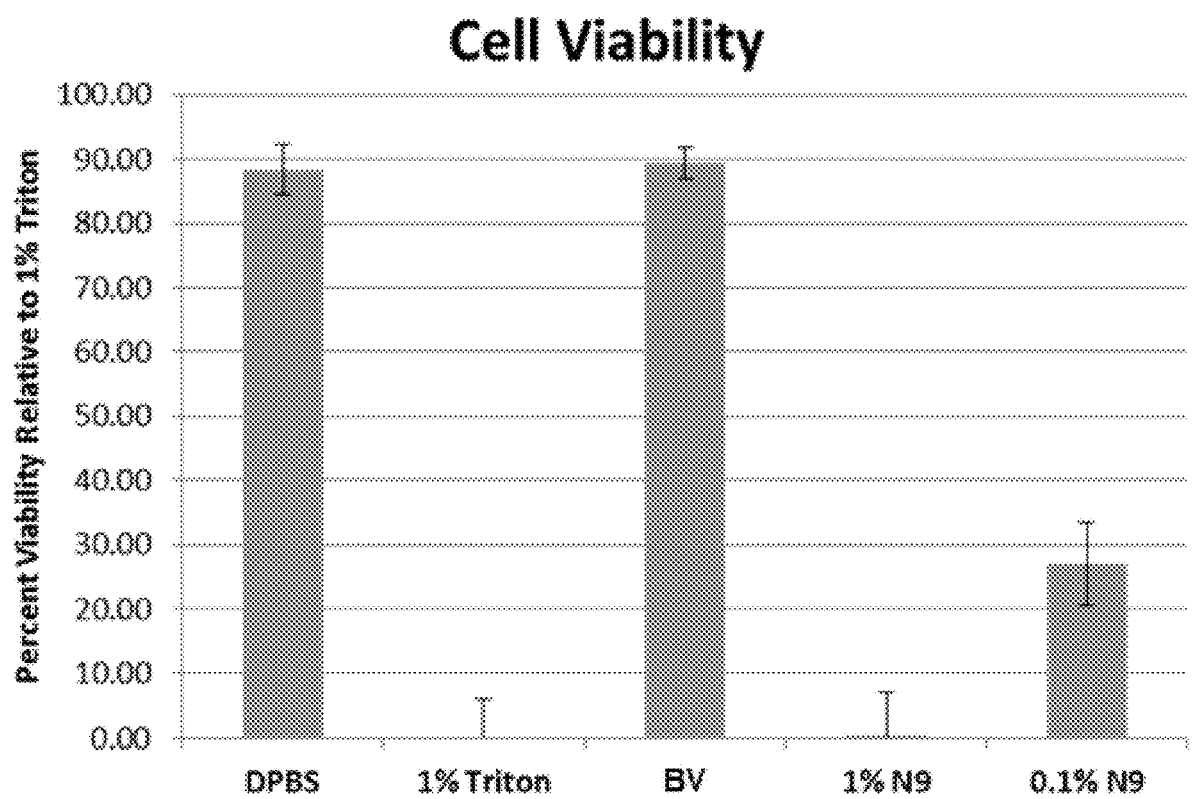
FIG. 2A illustrates cell viability following exposure of human-derived vaginal epithelial tissue culture cells to a bacterial vaginosis formulation (BV) for 24 hours, as compared to control compositions, including Dulbecco's phosphate-buffered saline (DPBS), 1% Triton, and nonoxynol 9 (N9) at 1% or 0.1%.

As shown in FIG. 2A, the formulation shows negligible toxicity to epithelial cells following direct contact with the formulation, demonstrated by lactate dehydrogenase (LDH) release in culture medium following exposure for 24 hours. LDH is a common marker of tissue damage. The percent viability shown in FIG. 2A is relative to 1% Triton. DPBS is a control sample treated with Dulbecco's phosphate buffered saline, which has no cytotoxic effect on the cells. 1% Triton is a control treatment that lyses cells, and is therefore toxic to cells. BV represents the bacterial vaginosis formulation described in Example 1. N9 is nonoxynol 9, used at 1% and at 0.1%, and is a surfactant that attacks cell membranes, and is commonly used in contraceptives.

Figure 2B:
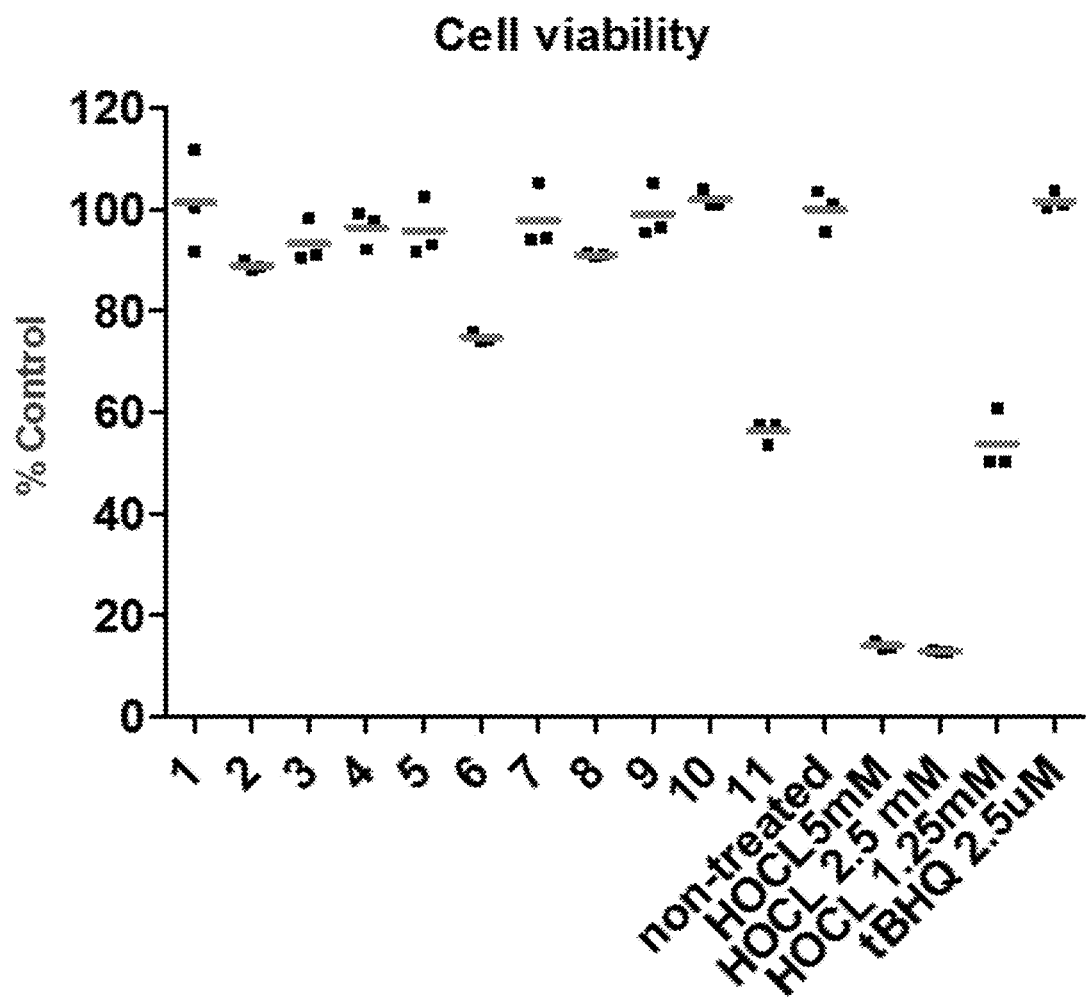
FIG. 2B illustrates exposure of human-derived vaginal epithelial tissue culture cells with various compositions for 24 hours. Samples 1-11 represent various bacterial vaginosis formulations as described herein. Non-treated sample includes treatment with medium alone, but no additional components. HOCL represents treatment with hypochlorous acid compositions at various concentrations. tBHQ represents treatment with tertiary butylhydroquinone.

As shown in FIG. 2B, the cell viability of the cell culture remained elevated for samples 1-11, indicating that the bacterial vaginosis formulation does not elicit cell toxicity.

Example 4

Inflammatory Response to Bacterial Vaginosis Formulations

The following example describes results of studies to determine the inflammatory response of bacterial vaginosis formulations.

MatTek EpiVaginal™ tissue culture model was exposed to the formulation described in Example 1 to determine the inflammatory response of the culture to the formulation.

Figure 3:
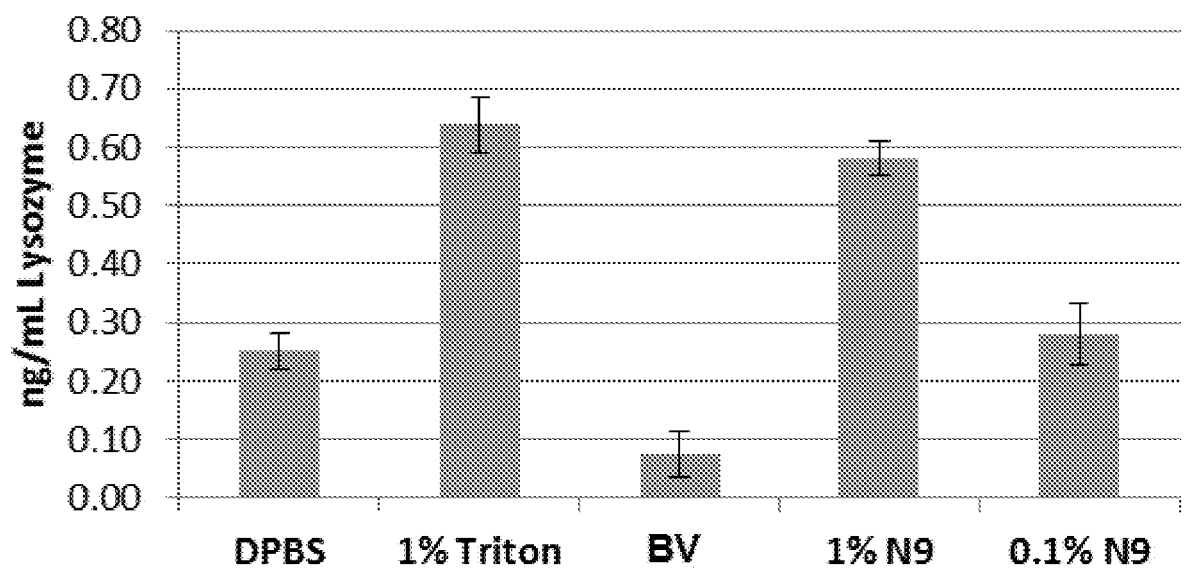
FIG. 3 illustrates a reduction in lysozyme secretion in human-derived vaginal epithelial tissue culture cells following exposure to BV for 24 hours, as compared to control compositions described in FIG. 2.

As shown in FIG. 3, the quantity of lysozyme secretion into culture medium is decreased compared to control levels, as measured by ELISA. Lysozyme is part of the innate immune system, and is a natural protectant against pathogens. Lysozyme secretion is indicative of pathogenic infection and indicates a proactive immune response.

Figure 4:
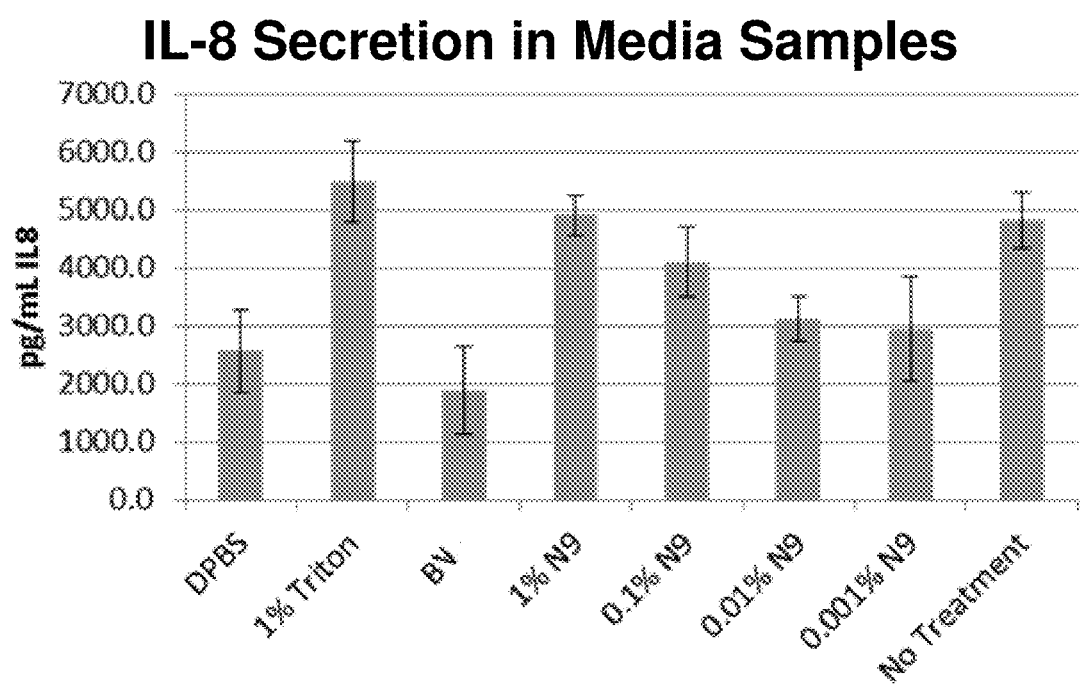
FIG. 4 illustrates a reduction in IL-8 secretion in human-derived vaginal epithelial tissue culture cells following exposure to BV for 24 hours, as compared to control compositions described in FIG. 2.

As shown in FIG. 4, the quantity of IL-8 secretion into culture medium is decreased in culture sample exposed to bacterial vaginosis formulations compared to control levels. IL-8 is a pro-inflammatory cytokine. Reduced secretion of IL-8 and lysozyme is indicative of a reduced inflammatory response in the vaginal microenvironment.

Example 5

Bacterial Toxicity Bacterial Vaginosis Formulations

The following example describes results of studies to determine bacterial toxicity of bacterial vaginosis formulations.

The bacterial vaginosis formulation of Example 1 was used against various pathogens to determine the toxicity against the pathogens. HIV-1 strain HTLV III$_B$ was exposed to the bacterial vaginosis formulation for an exposure time of either 5 minutes or 10 minutes at a temperature of 20.0° C. in the presence of a 5% FBS organic soil load. The formulation demonstrated a greater than 99.99% reduction in viral titer following 5 and 10 minute exposure times to HIV-1, as compared to the titer of the corresponding virus control. The 50% tissue culture infective dose (TCID$_{50}$)/200 µL, a measure of infectious virus titer, was less than $10^{2.50}$ at both 5 and 10 minutes. Table 3 summarizes the effects of exposure of the formulation to a suspension of HIV-1. The cytotoxicity and neutralization control results are presented in Table 4. MT-2 (human T cell leukemia cells) were used as indicator cell cultures.

TABLE 3

Effects of Formulation Against HIV-1 in Suspension

| | Virus Control | | HIV-1 + Formulation | |
|---|---|---|---|---|
| Dilution | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | T T T T | T T T T |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + + + | 0 0 0 0 | 0 0 0 0 |
| $10^{-7}$ | 0 0 0 0 | 0 0 0 0 | 0 0 0 0 | 0 0 0 0 |
| $TCID_{50}/200\ \mu L$ | $10^{6.50}$ | $10^{6.50}$ | $\leq 10^{2.50}$ | $\leq 10^{2.50}$ |
| Percent Reduction | | | ≥99.99% | ≥99.99% |
| Log Reduction | | | ≥4.00 $\log_{10}$ | ≥4.00 $\log_{10}$ |

(+) = positive test for the presence of test virus
(0) = no test virus recovered and/or no cytotoxicity present
(T) = cytotoxicity present

TABLE 4

Cytotoxicity and Neutralization Results for HIV-1

| Dilution | Cytotoxicity Control Formulation | Neutralization Control HIV-1 + Formulation |
|---|---|---|
| Cell Control | 0 0 0 0 | 0 0 0 0 |
| $10^{-2}$ | T T T T | T T T T |
| $10^{-3}$ | 0 0 0 0 | + + + + |
| $10^{-4}$ | 0 0 0 0 | + + + + |
| $10^{-5}$ | 0 0 0 0 | + + + + |
| $10^{-6}$ | 0 0 0 0 | + + + + |
| $10^{-7}$ | 0 0 0 0 | + + + + |
| $TCID_{50}/200\ \mu L$ | $10^{2.50}$ | *Neutralized at ≤2.50 $\log_{10}$ |

(+) = positive test for the presence of test virus
(0) = no test virus recovered and/or no cytotoxicity present
(T) = cytotoxicity present (*)=Neutralization control reported as $TCID_{50}/250\ \mu L$ HSV-2, ATCC VR-734, Strain G was exposed to the formulation for either 5 minutes or 10 minutes at a temperature of 21.0° C. in the presence of a 5% FBS organic soil load. The formulation demonstrated a greater than 99.9997% reduction in viral titer following 5 minute exposure time and a greater than 99.998% reduction in viral titer following a 10 minute exposure time to HSV-2, as compared to the titer of the corresponding virus control. The log reductions in viral titer were greater than 5.50 $\log_{10}$ and greater than 4.75 $\log_{10}$, respectively. Table 5 summarizes the effects of exposure of the formulation to a suspension of HSV-2. The cytotoxicity and neutralization control results are presented in Table 6. Vero cells were used as indicator cell cultures.

TABLE 5

Effects of Formulation Against HSV-2 in Suspension

| | Virus Control | | HSV-2 + Formulation | |
|---|---|---|---|---|
| Dilution | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + 0 + + | 0 0 0 0 | 0 0 0 0 |
| $10^{-7}$ | + 0 + 0 | 0 0 0 0 | 0 0 0 0 | 0 0 0 0 |
| $10^{-8}$ | 0 0 0 0 | 0 0 0 0 | 0 0 0 0 | 0 0 0 0 |
| $TCID_{50}/100\ \mu L$ | $10^{7.00}$ | $10^{6.25}$ | $\leq 10^{1.50}$ | $\leq 10^{1.50}$ |
| Percent Reduction | | | ≥99.9997% | ≥99.998% |
| Log Reduction | | | 5.50 $\log_{10}$ | 4.75 $\log_{10}$ |

(+) = positive test for the presence of test virus
(0) = no test virus recovered and/or no cytotoxicity present

TABLE 6

Cytotoxicity and Neutralization Results for HSV-2

| Dilution | Cytotoxicity Control Formulation | Neutralization Control HSV-2 + Formulation |
|---|---|---|
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID50/100\ \mu L$ | $\leq 10^{1.50}$ | *Neutralized at ≤1.50 $\log_{10}$ |

(+) = positive test for the presence of test virus
(0) = no test virus recovered and/or no cytotoxicity present
*= Neutralization control reported as $TCID_{50}/100\ \mu L$ Duck HBV was exposed to the formulation for either 5 minutes or 10 minutes at a temperature of 20.0° C. in the presence of 100% duck serum, with no additional soil load added. The formulation demonstrated a greater than 99.999% reduction in viral titer following 5 minute exposure time and a greater than 99.998% reduction in viral titer following a 10 minute exposure time to duck HBV, as compared to the titer of the corresponding virus control. The log reductions in viral titer were greater than 5.00 $\log_{10}$ and greater than 4.75 $\log_{10}$, respectively. Table 7 summarizes the effects of exposure of the formulation to a suspension of HSV-2. The cytotoxicity and neutralization control results are presented in Table 8. Primary duck hepatocytes were used as indicator cell cultures.

TABLE 7

Effects of Formulation Against HBV in Suspension

| | Virus Control | | HBV + Formulation | |
|---|---|---|---|---|
| Dilution | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + + 0 | 0 0 0 0 | 0 0 0 0 |
| $10^{-7}$ | 0 0 0 0 | 0 0 0 0 | 0 0 0 0 | 0 0 0 0 |
| $TCID_{50}/250\ \mu L$ | $10^{6.50}$ | $10^{6.25}$ | $\leq 10^{1.50}$ | $\leq 10^{1.50}$ |
| Percent Reduction | | | ≥99.999% | ≥99.998% |
| Log Reduction | | | ≥5.00 $\log_{10}$ | ≥4.75 $\log_{10}$ |

(+) = positive test for the presence of test virus
(0) = no test virus recovered and/or no cytotoxicity present

TABLE 8

Cytotoxicity and Neutralization Results for HBV

| Dilution | Cytotoxicity Control Formulation | Neutralization Control HBV + Formulation |
|---|---|---|
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID_{50}/250\ \mu L$ | $\leq 10^{1.50}$ | *Neutralized at $\leq 1.50\ Log_{10}$ |

(+) = positive test for the presence of test virus
(0) = no test virus recovered and/or no cytotoxicity present
*= Neutralization control reported as $TCID_{50}/250\ \mu L$

*Chlamydia trachomatis* (Serotype K), ATCC VR-887, strain UW-31/Cx was exposed to the formulation for either 5 minutes or 10 minutes at a temperature of 20.0° C. in the presence of 5% FBS organic soil load. The formulation demonstrated a greater than 99.999% reduction in *Chlamydia* titer following 5 minute exposure time and a greater than 99.998% reduction in *Chlamydia* titer following a 10 minute exposure time to *Chlamydia trachomatis* (Serotype K), as compared to the titer of the corresponding *Chlamydia* control. The log reductions in *Chlamydia* titer were greater than 5.00 $log_{10}$ and greater than 4.75 $log_{10}$, respectively. Table 9 summarizes the effects of exposure of the formulation to a suspension of *Chlamydia*. The cytotoxicity and neutralization control results are presented in Table 10.

TABLE 9

Effects of Formulation Against *Chlamydia* in Suspension

| | *Chlamydia* Control | | *Chlamydia trachomatis* + Formulation | |
|---|---|---|---|---|
| Dilution | 5 minute exposure | 10 minute exposure | 5 minute exposure | 10 minute exposure |
| Cell Control | 0 0 0 0 | 0 0 0 0 | 0 0 0 0 | 0 0 0 0 |
| $10^{-2}$ | + + + + | + + + + | 0 0 0 0 | 0 0 0 0 |
| $10^{-3}$ | + + + + | + + + + | 0 0 0 0 | 0 0 0 0 |
| $10^{-4}$ | + + + + | + + + + | 0 0 0 0 | 0 0 0 0 |
| $10^{-5}$ | + + + + | + + + + | 0 0 0 0 | 0 0 0 0 |
| $10^{-6}$ | + + + + | + + 0 + | 0 0 0 0 | 0 0 0 0 |
| $10^{-7}$ | 0 0 0 0 | 0 0 0 0 | 0 0 0 0 | 0 0 0 0 |
| $TCID_{50}/200\ \mu L$ | $10^{6.50}$ | $10^{6.25}$ | $\leq 10^{1.50}$ | $\leq 10^{1.50}$ |
| Percent Reduction | | | $\geq 99.999\%$ | $\geq 99.998\%$ |
| Log Reduction | | | $\geq 5.00\ log_{10}$ | $\geq 4.75\ log_{10}$ |

(+) = positive test for the presence of test *chlamydia*
(0) = no test *chlamydia* recovered and/or no cytotoxicity present

TABLE 10

Cytotoxicity and Neutralization Results for *Chlamydia*

| Dilution | Cytotoxicity Control Formulation | Neutralization Control *Chlamydia trachomatis* + Formulation |
|---|---|---|
| Cell Control | 0 0 0 0 | 0 0 0 0 |
| $10^{-2}$ | 0 0 0 0 | + + + + |
| $10^{-3}$ | 0 0 0 0 | + + + + |
| $10^{-4}$ | 0 0 0 0 | + + + + |
| $TCID_{50}/100\ \mu L$ | $\leq 10^{1.50}$ | *Neutralized at $\leq 1.50\ Log_{10}$ |

(+) = positive test for the presence of test *chlamydia*
(0) = no test *chlamydia* recovered and/or no cytotoxicity present
*= Neutralization control reported as $TCID_{50}/200\ \mu L$

*Neisseria gonorrhoeae* was evaluated in a time kill assay. *Neisseria gonorrhoeae*, ATCC 43069, was exposed to the formulation at exposure times of 1, 2, 5, and 10 minutes in suspension at a temperature of 21.0° C. Suspensions of *Neisseria* gonorrhoeae (ATCC 43069) were prepared by diluting the *Neisseria gonorrhoeae* in test medium (Minimum Essential Medium (MEM) supplemented with 10% (v/v) heat-inactivated fetal bovine serum (FBS), 2 µg/ml cycloheximide, 4.5 g/L glucose, 10 mM HEPES, 10 µg/ml gentamicin, and 2.5 µg/mL amphotericin B). Undiluted formulation was added to each suspension and allowed to incubate at 21.0° C. Aliquots were removed at 1 minute, 2 minutes, 5 minutes and 10 minutes, neutralized by serial dilution in test medium, and assayed for the presence of *Neisseria gonorrhoeae*. Culture purity, neutralizer sterility, test population, and neutralization confirmation controls were performed in parallel. McCoy cells were used as the indicator cell culture.

After exposure, an aliquot of the suspension was transferred to a neutralizer and was assayed for survivors. Appropriate culture purity, neutralizer sterility, test population, and neutralization confirmation controls were performed. The neutralizer was Letheen broth with 0.07% lecithin and 0.5% Tween 80. The neutralizer sterility control shows no growth of *Neisseria gonorrhoeae*. The control population of *Neisseria gonorrhoeae* shows $3.2 \times 10^4$ colony forming units, and log reduction of 4.51 $log_{10}$. The exposure of *Neisseria gonorrhoeae* to the formulation for any of 1, 2, 5, and 10 minutes showed no survivors at any dilution. Table 11 summarizes the effects of exposure for bacterial vaginosis formulations against *Neisseria gonorrhoeae*.

TABLE 11

Formulation Against *Neisseria gonorrhoeae*

| Exposure Time (minutes) | CFU/mL in Test population control ($Log_{10}$) | CFU/mL of Survivors | $Log_{10}$ Survivors | Percent Reduction | $Log_{10}$ Reduction |
|---|---|---|---|---|---|
| 1 | $3.2 \times 10^4$ (4.51) | <5 | <0.70 | >99.9% | >3.81 |
| 2 | | <5 | <0.70 | >99.9% | >3.81 |
| 5 | | <5 | <0.70 | >99.9% | >3.81 |
| 10 | | <5 | <0.70 | >99.9% | >3.81 |

CFU = colony forming units

Table 12 summarizes the results, showing the efficacy of the formulation in reducing a variety of organismal populations.

TABLE 12

Bacterial Vaginosis Formulation Destroys Major Sexually Transmitted Infections

| Test Organism | Max Control Population | Population at 5 minute exposure | Percent Reduction | Population at 10 minute exposure | Percent Reduction |
|---|---|---|---|---|---|
| HIV-1 | 4.00 Log10 | 0 | >99.99% | 0 | >99.99% |
| Herpes simplex virus type 2 | 5.50 Log10 | 0 | >99.9997% | 0 | >99.998% |
| Hepatitis B virus | 5.00 Log10 | 0 | >99.999% | 0 | >99.998% |
| Chlamydia trachomatis | 5.00 Log10 | 0 | >99.999% | 0 | >99.998% |
| Neisseria gonorrhoeae | 3.8 Log10 | 0 | >99.9% | 0 | >99.9% |

This example demonstrates that the formulation is capable of significantly reducing the risk of STI infection transmission. Additional tests were similarly performed on other organisms, and show that the formulations described herein have germicidal activity against S. aureus, E. coli, P. aeruginosa, C. albicans, and A. niger in 14 and 28-day challenge models. These tests demonstrated <10 CFU outgrowth from a $10^5$-$10^6$ CFU initial seeding challenge. These results indicate that the formulations function as a broad spectrum microbicide.

Example 6

Bacterial Toxicity Bacterial Vaginosis Formulations

The following example describes results of studies to determine bacterial toxicity of bacterial vaginosis formulations.

The bacterial vaginosis formulation of Example 1 was used against Staphylococcus aureus and Pseudomonas aeruginosa to determine the toxicity against these pathogens. These pathogens were evaluated in a time kill assay. Each pathogen was exposed to a bacterial vaginosis formulation at 2×MIC and 4×MIC under isotonic and hypertonic conditions. Results of the time kill assay are shown in Table 13. Results shown are average values for two separate cultures, each culture sampled and measured three times.

TABLE 13

Formulation Against S. aureus and P. aeruginosa

| Exposure Time (seconds) | CFU/mL at 2 × MIC Isotonic | | CFU/mL at 4 × Isotonic | |
|---|---|---|---|---|
| | S. aureus | P. aeruginosa | S. aureus | P. aeruginosa |
| 0 | 5,500,000 | 4,500,000 | 3,350,000 | 1,925,000 |
| 5 | 1,867 | 1,467 | 908 | 4,857 |
| 10 | 1,117 | 883 | 625 | 2,833 |
| 30 | 500 | 400 | 533 | 500 |
| 60 | 150 | 133 | 250 | 267 |
| 120 | 117 | 100 | 100 | 183 |

| Exposure Time (seconds) | CFU/mL at 2 × MIC Hypertonic | | CFU/mL at 4 × Hypertonic | |
|---|---|---|---|---|
| | S. aureus | P. aeruginosa | S. aureus | P. aeruginosa |
| 0 | 6,000,000 | 4,000,000 | 3,200,000 | 1,775,000 |
| 5 | 983 | 1,473 | 692 | 367 |
| 10 | 450 | 850 | 550 | 283 |
| 30 | 333 | 833 | 550 | 233 |
| 60 | 200 | 200 | 350 | 250 |
| 120 | 133 | 167 | 267 | 200 |

In addition, sputum samples were obtained from subjects having an infection of S. aureus and/or P. aeruginosa, and each sample was exposed to a bacterial vaginosis formulation having 200 ppm hypochlorite. Results of the sputum sample experiment are shown in Table 14. The results show average results across 18 samples for S. aureus and 20 samples for P. aeruginosa, each sample assayed separately two or three times.

TABLE 14

Formulation Against S. aureus and P. aeruginosa in Sputum Samples

| | Isotonic | | | Hypertonic | | |
|---|---|---|---|---|---|---|
| Bacteria | No treatment | Treatment | % Killed | No treatment | Treatment | % Killed |
| S. aureus (CFU/mL) | 115,020,872 | 6,762,879 | 94.12 | 64,355,000 | 944,368 | 98.53 |
| P. aeruginosa (CFU/mL) | 10,833,635 | 731,269 | 93.25 | 17,006,019 | 569,331 | 96.65 |

Example 7

Anti-Oxidant Responses with Bacterial Vaginosis Formulations

The following example describes results of studies to determine the anti-oxidant response following treatment with bacterial vaginosis formulations.

MatTek EpiVaginal™ tissue culture model was exposed to the formulation described in Example 1 to determine the anti-oxidant response of the culture following exposure to the formulation.

Figure 5:
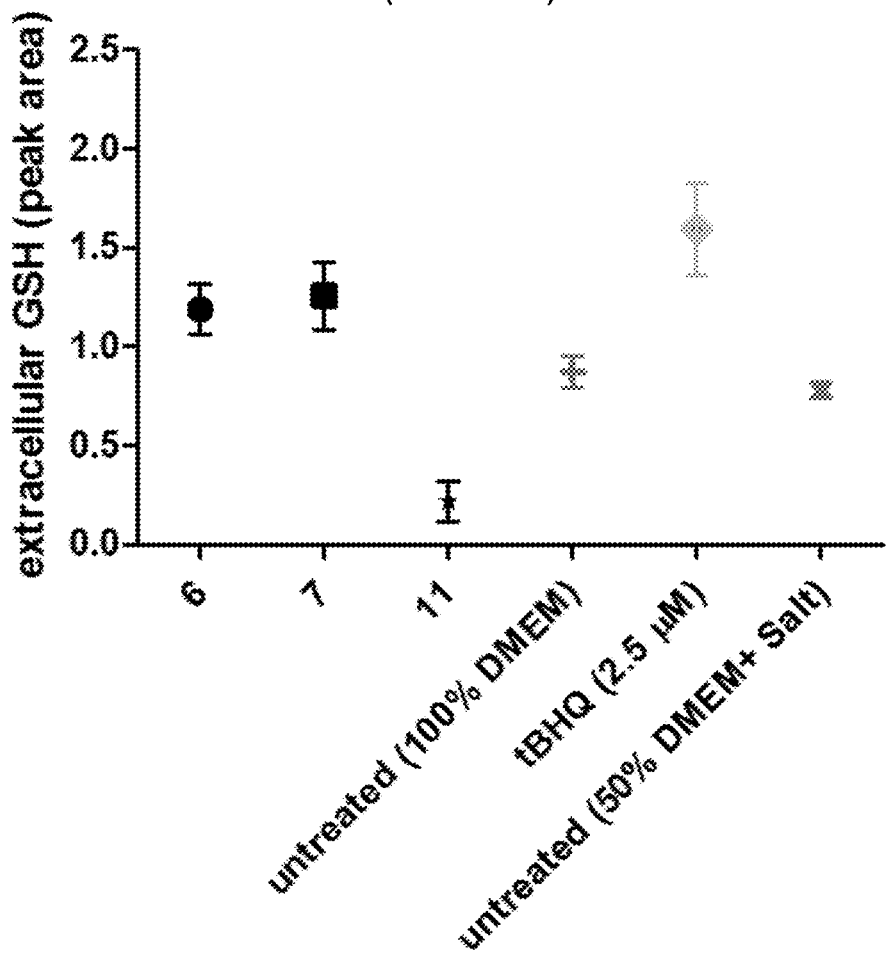
FIG. 5 illustrates reduction in glutathione (GSH) secretion in human-derived vaginal epithelial tissue culture cells following exposure to BV for 24 hours, as compared to control treatments, including tertiary butylhydroquinone (tBHQ), Dulbecco's minimal essential medium (DMEM).

As shown in FIG. 5, treatment with the formulation results in increased secretion of glutathione (GSH) in growth medium. tBHQ is a positive control treatment group. These data indicate that the formulation increases response activity by Nrf2, a global oxidative stress response transcription factor, and that the formulation primes the cells to provide strong anti-oxidant responses when exposed to conditions that may cause cellular damage.

Figure 6:
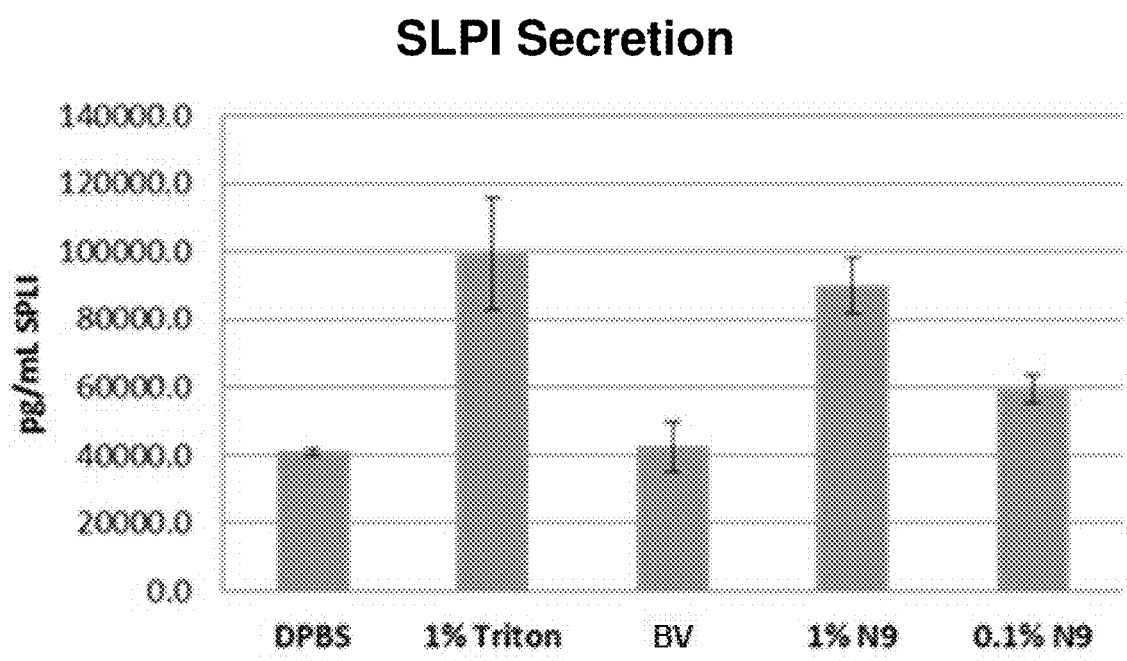
FIG. 6 illustrates reduction in secretory leukocyte protease inhibitor (SLPI) secretion in human-derived vaginal epithelial tissue culture cells following exposure to BV for 24 hours, as compared to control compositions described in FIG. 2.

In addition, FIG. 6 shows the secretion of secretory leukocyte protease inhibitor (SLPI) into culture medium. SLPI is a secreted protease involved with proteolytic cleavage of viral particles. An elevated level of SLPI is indicative of inflammatory and oxidative stress in cells. As shown in FIG. 6, the bacterial vaginosis formulation does not increase secretion of SLPI in culture.

Example 8

Bacterial Vaginosis Formulations in Animal Models

The following example describes studies to determine the efficacy of the bacterial vaginosis formulations described herein on mouse models.

All procedures involving mice are approved and carried out according to NIH recommended procedures and precautions. Mice are housed at a maximum of two per cage, under standard room conditions, with ad libidum food and water. Every effort is made to minimize animal suffering. The mice are estradiol treated to induce estrus, thereby making the mouse vagina susceptible to gonococcal or chlamydial infection. Following induction, mice are challenged with the bacteria to initiate infection in the presence or absence of human Lactobacilli Immediately following, the bacterial vaginosis formulations are applied and vaginal washes are analyzed for the outgrowth of microorganisms. These experiments are performed in the presence of human *Lactobacillus* species as well to evaluate the ability of the formulations to kill off pathogenic organisms while allowing for the survival of the beneficial Lactobacilli species necessary for vaginal health.

The inherent microbicide activity of the formulations results in elimination of gonococcal and Chlamydial seeded organisms, and have no effect on the seeded *Lactobacillus*. The *Lactobacillus* produces normal amounts of lactic acid by fermentation and the pH of the vaginal environment remains hospitable to longer term colonization by *Lactobacillus*. Accordingly, the compositions described herein are safe for female lactobacilli flora.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of promoting vaginal health in a subject, comprising:
   topically administering to a vaginal region of a subject a composition comprising:
   a reactive oxygen species;
   a rheology agent;
   a silicone polymer; and
   hydrochloric acid,
   wherein the composition has a pH ranging from about 6.0 to about 7.5,
   whereby, topically administering the composition promotes a healthy vaginal microenvironment by maintaining healthy vaginal microbiota.

2. The method of claim 1, wherein topically administering the composition prevents or treats bacterial vaginosis.

3. The method of claim 1, wherein the reactive oxygen species is hypochlorite.

4. The method of claim 1, wherein the reactive oxygen species is present in an amount of about 50 to about 100 ppm.

5. The method of claim 1, wherein the reactive oxygen species is present in an amount of about 60 ppm.

6. The method of claim 1, wherein the rheology agent is sodium magnesium silicate.

7. The method of claim 1, wherein the rheology agent is present in an amount of about 0.1%, 0.25%, 0.5%, 0.75%, 1%, 1.5%, 2%, 2.5%, 3%, 3.5%, 4%, 4.5%, 5%, 6%, 7%, 10%, or 15% w/v.

8. The method of claim 1, wherein the rheology agent is present in an amount of about 3% w/v.

9. The method of claim 1, wherein the silicone polymer is dimethicone.

10. The method of claim 1, wherein the silicone polymer is present in an amount of about 0.5%, 1%, 5%, 10%, 15%, 20%, 30%, 40%, or 50% w/v.

11. The method of claim 1, wherein the silicone polymer is present in an amount of about 10% w/v.

12. The method of claim 1, wherein the pH adjuster is present in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% w/v.

13. The method of claim 1, wherein the pH adjuster is present in an amount of about 0.08% w/v.

14. The method of claim 1, wherein the composition further comprises water.

15. The method of claim 1, wherein the composition comprises hypochlorite in an amount of about 60 ppm, sodium magnesium silicate in an amount of about 3% w/v, dimethicone in an amount of about 10% w/v, hydrochloric acid in an amount of about 0.08% w/v, and water in an amount of about 90% w/v.

16. The method of claim 1, wherein the healthy vaginal microbiota comprises bacteria of the genus *Lactobacillus*.

17. The method of claim 1, wherein topically administering the composition reduces secretion of pro-inflammatory cytokines from vaginal epithelial.

18. The method of claim 17, wherein the pro-inflammatory cytokines is IL-8.

19. The method of claim 1, wherein topically administering the composition prevents an inflammatory response in a vaginal microenvironment.

20. The method of claim 1, wherein topically administering the composition activates a nuclear factor-like 2 (Nrf2) related pathway.

21. The method of claim 20, wherein the activation of Nrf2 related pathway prevents oxidative damage.

22. The method of claim 1, wherein the administration of the composition increases glutathione secretion in the vaginal microenvironment.

23. The method of claim 1, wherein topically administering the composition reduces abnormal vaginal microflora comprising *Gardnerella vaginalis, Atopobium vaginae, Megasphaera*, or BVAB2.

* * * * *